US010525126B2

(12) United States Patent
Silhavy et al.

(10) Patent No.: US 10,525,126 B2
(45) Date of Patent: Jan. 7, 2020

(54) MODIFIED LIPOPOLYSACCHARIDE GLYCOFORM AND METHOD OF USE

(71) Applicant: The Trustees of Princeton University, Princeton, NJ (US)

(72) Inventors: Thomas J. Silhavy, Belle Mead, NJ (US); Marcin Grabowicz, Princeton, NJ (US); Daniel Kahne, Brookline, MA (US); Matthew Lebar, Mandeville, LA (US); Dorothee Andres, Potsdam (DE)

(73) Assignees: THE TRUSTEES OF PRINCETON UNIVERSITY, Princeton, NJ (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 98 days.

(21) Appl. No.: 15/586,781

(22) Filed: May 4, 2017

(65) Prior Publication Data
US 2017/0239350 A1 Aug. 24, 2017

Related U.S. Application Data

(62) Division of application No. 14/707,718, filed on May 8, 2015, now Pat. No. 9,677,052.

(60) Provisional application No. 62/098,014, filed on Dec. 30, 2014, provisional application No. 61/991,116, filed on May 9, 2014.

(51) Int. Cl.
*A61K 39/39* (2006.01)
*C12N 9/00* (2006.01)
*C07H 13/06* (2006.01)
*C12P 21/00* (2006.01)
*C07H 15/04* (2006.01)
*C07K 4/00* (2006.01)
*C12N 15/04* (2006.01)
*A61K 39/00* (2006.01)

(52) U.S. Cl.
CPC ............. *A61K 39/39* (2013.01); *C07H 13/06* (2013.01); *C07H 15/04* (2013.01); *C07K 4/00* (2013.01); *C12N 9/00* (2013.01); *C12N 9/93* (2013.01); *C12N 15/04* (2013.01); *C12P 21/005* (2013.01); *A61K 2039/55516* (2013.01); *A61K 2039/55572* (2013.01); *A61K 2039/55583* (2013.01); *A61K 2039/55594* (2013.01)

(58) Field of Classification Search
None
See application file for complete search history.

(56) References Cited

PUBLICATIONS

Zhou, Z. et al. "Function of *Escherichia coli*MsbA, an Essential ABC Family Transporter, in Lipid A and Phospholipid Biosynthesis", The Journal of Biological Chemistry (1998) vol. 273, pp. 12466-12475.
Szwedziak, P. & Lowe, J. "Do the Divisome and Elongasome Share a Common Evolutionary Past?", Current Opinion in Microbiology (2013) vol. 16, pp. 745-751.
Tsai, C. & Frasch, C. "A Sensitive Silver Stain for Detecting Lipopolysaccharides in Polyacrylamide Gels", Analytical Biochemistry, (1981) vol. 119, pp. 115-119.
Typas, A. et al, "Regulation of Peptidoglycan Synthesis by Outer-Membrane Proteins", Cell (2010) vol. 143, pp. 1097-1109.
Typas, A. et al, "From the Regulation of Peptidoglycan Synthesis to Bacterial Growth and Morphology", National Review of Microbiology (2012) vol. 10, pp. 123-126.
Uehara, T. et al., "Lyt-M Domain Factors are Required for Daughter Cell Separation and Rapid Ampicillin-Induced Lysis in *Escherichia coli*", Journal of Bacteriology (2009) vol. 1941, pp. 5094-5107.
Van Heijenoort, et al. "Membrane Intermediates in the Peptidoglycan Metabolism of *Exherichia-coli*: Possible Roles of PBP 1b and PBP3", Journal of Bacteriology (1992) vol. 32, pp. 149-167.
Vollmer, W. et al., "Peptidoglycan Structure and Architecture", FEMS Microbiology Reviews (2008) vol. 32, pp. 149-167.
Wang, X. et al. "MsbA Transporter-Dependent Lipid A 1 Dephosphorylation on the Periplasmic Surface of the Inner Membrane: Topography of Francisella Novicida LpxE Expressed in *Escherichia coli*", Journal of Biological Chemistry vol. 279, pp. 49470-49478.
Wang, L et al. "The Variation of O Antigens in Gram Negative Bacteria Subcell", Biochemistry (2010) vol. 53, pp. 123-152.
Wu, T. et al., "Identification of a Protein Complex that Assembles Lipopolysaccharide in the Outer Membrane of *Escherichia coli*", Proceedings of the National Academy of Sciences, vol. 103, pp. 114754-114759.
Wu, T. et al, "Identification of a Multicomponent Complex Required for Outer Membrane Biogenesis in *Escherichia coli*", Cell (2005) vol. 121, pp. 235-245.
AL-Kaddah et al., "Analysis of Membrane Interactions of Antibiotic Peptides using ITC and Biosensor Measurements." Biophysical Chemistry (2010), vol. 152, pp. 145-152.
Baba, T. et al., "Construction of *Escherichia coli* K-12 in-frame, Single Gene Knockout Mutants: The Keio Collection", Molecular Systems Biology (2006), Article 2006-2008.
Brill,J.A. et al, "Fine Structure Mapping and Identification of Two Regulators of Capsule Synthesis in *Escherichia coli* K-12", Journal of Bacteriology, Jun. 1988, vol. 170, No. 6, pp. 2599-2611.
Button, J. et al, "A Suppressor of Cell Death Caused by the Loss of [sigma] Downregulates Extracytoplasmic Stress Responses and Outer Membrane Vesicle Production in *Escherichia coli*", Journal of Bacteriology, Mar. 2007, vol. 198, No. 5, pp. 1523-1530.

(Continued)

Primary Examiner — Jennifer E Graser
(74) Attorney, Agent, or Firm — Meagher Emanuel Laks Goldberg & Liao, LLP

(57) ABSTRACT

The present disclosure generally relates to genetic engineering of bacteria. More particularly, the present disclosure describes genetic engineering of *E. coli* to create mutant O-antigen ligase, as well as novel lipopolysaccharide molecules resulting from that genetic engineering. Methods for using those novel molecules are also described.

12 Claims, 13 Drawing Sheets
Specification includes a Sequence Listing.

(56) References Cited

PUBLICATIONS

Casadaban, M., "Transposition and Fusion of the lac Genes to Selected Promoters in *Escherichia coli* using Bacteriophages Lamda and Mu", Journal of Molecular Biology (1976) vol. 104, pp. 541-555.

Chng, S.S. et al., "Characterization of the Two-Protein Complex in *Escherichia coli* Responsible for Lipopolysaccharide Assembly at the Outer Membrane", Proceedings of the National Academy of Sciences USA (2010) vol. 107, pp. 5363-5368.

Chng, S.S. et al, "Proteins Required for Lipopolysaccharide Assembly in *Esherichia coli* Form a Transenvelope Complex", Biochemistry (2010) vol. 49; pp. 4565-4567.

Cui, L. et al, "Cell Wall Thickening is a Common Feature of Vancomycin Resistance in *Staphylococcus aureus*" Journal of Clinical Microbiology (2003), vol. 41, pp. 5-14.

Darveau, R.P & Hancock, R.E., "Procedure of Isolation of Bacterial Lipopolysaccharides from both Smooth and Rough Pseudomona Aeruginosa and *Salmonella typhimurium* Strains", Journal of Bacteriology (1983), vol. 155 No. 2, pp. 831-838.

Eggert, U. et al. "Genetic Basis for Activity Differences Between Vancomycin and Glycolipid Derivatives of Vancomycin", Science (2001), vol. 294, pp. 361-364.

Faridmoayer, A. et al., "Extreme Substrate Promiscuity of the Neisseria Oligosaccharyl Transferase Involved in Protein O-Glycosylation" The Journal of Biological Chemistry, Dec. 2008, vol. 283, No. 50, pp. 34596-34604.

Fritz, J. et al. "Synergistic Stimulation of Human Monocytes and Dendrtic Cells by Toll-Like Receptor 4 and NOD1- and NOD2— Activating Agonists" European Journal of Immunology (2005), vol. 35, pp. 2459-2470.

Galanos C. et al. "A New Method of the Extraction of R Lipopolysaccharides", European Jounal of Biochemistry (1969) vol. 9, pp. 245-249.

Glauner, B. et al. "The Composition of the Murein of *Escherichia coli*", The Journal of Biological Chemistry, Jul. 1988, vol. 263, No. 21, pp. 10088-10095.

Gozdziewicz, T. et al. "First Evidence of a Covalent Linkage between Enterobacterial Common Antigen and Lipopolysaccharide in Shigella Sonnei Phase II ECALPS", The Journal for Biological Chemistry, Jan. 31, 2014, vol. 289, No. 5, pp. 2745-2754.

Gottesman, S. et al. "Regulation of Capsular Polysaccharide Synthesis in *Escherichia coli* K-12: Characterization of Three Regulatory Genes", Journal of Bacteriology, Jun. 1985, vol. 162, No. 3, pp. 1111-1119.

Han, W. et al. "Defining Function of Lipopolysaccharide O-antigen Ligase WaaL Using Chemoenzymatically Synthesized Substrates", The Journal of Biological Chemistry, Feb. 17, 2012, vol. 287, No. 8, pp. 5357-5365.

Islam, S. et al. "Membrane Topology Mapping of the O-Antigen Flippase (Wzx) Polymerase (Wzy), and Ligase (WaaL) from Pseudomonas Aeruginosa PAO1 Reveals Novel Domain Architecture", MBio, Jul./Aug. 2010, vol. 1, Issue 3.

Kalynych, S. et al. "Progress in Understanding the Assembly Process of Bacterial O-Antigen" Federation of European Microbiology Societies (2014) vol. 38, pp. 1048-1065.

Kamio, Y & Nikaido H., "Outer Membrane of *Salmonella typhimuririum*: Accessibility of Phospholipid Head Groups to Phospholipase C and Cyanogen Bromide Activated Dextran in the External Medium", Biochemistry (1976) vol. 15, No. 12, pp. 2561-2570.

Kitagawa, M. et al. "Complete Set of ORF Clones of *Escherichia coli* ASKA Library (A Complete Set of *E. coli* K-12 Archive: Unique Resources for Biological Research", DNA Research (2005) vol. 12, pp. 291-299.

Kleckner, N. et al. "Uses of Transposons with Emphasis on Tn10", Methods in Enzymology (1991) vol. 204, pp. 139-180.

Lebar, M. et al. "Forming Cross-Linked Peptidoglycan from Synthetic Gram-Negative Lipid II", Journal of the American Chemical Society (2013).

Lee, T. et al. "A Dynamically Assembled Cell Wall Synthesis Machinery Buffers Cell Growth", Proceedings of the National Academy of Sciences, Mar. 25, 2014, vol. 111, No. 12, pp. 4554-4559.

Lima, S. et al. "Dual Molecular Signals Mediate the Bacterial Response to Outer-Membrane Stress", Science, May 17, 2013, vol. 340, pp. 837-841.

Liu, D. & Reeves, P. "*Escherichia coli* K-12 Regains its O-Antigen", Microbiology (1994) vol. 140, pp. 49-57.

Malojcic, G. et al. "LptE Binds to and Alters the Physical State of LPS to Catalyze its Assembly at the Cell Surface", Proceedings of the National Academy of Sciences of USA, Jul. 14, 2014, vol. 111, No. 26, pp. 9467-9472.

Mata-Haro, V. et al. "The Vaccine Adjuvant Monophosphoryl Lipid A as a TRIF-Biased Agnoist of TJR4", Science, Jun. 15, 2007, vol. 316, pp. 1628-1632.

Meier-Dieter, U. et al. "Biosynthesis of Enterobacterial Common Antigen in *Escherichia coli*: Biochemical Characterization of the Tn10 Insertion Mutants Defective in Enterobacterial Common Antigen Synthesis", The Journal of Biological Chemistry, Aug. 15, 1990, vol. 265, No. 23, pp. 13490-13497.

Meredith, T. et al. "Modification of Lipopolysaccharide with Colanic Acid (M-Antigen) Repeats in *Escherichia coli*", The Journal of Biological Chemistry, Mar. 16, 2007, vol. 282, No. 11, pp. 7790-7798.

Mohammadi, T. et al. "Identification of FtsW as a Transporter of Lipid Linked Cell Wall Precursors Across the Membrane", The EMBO Journal (2011), vol. 30, No. 8, pp. 1425-1432.

Nikaido, H. "Molecular Basis of Bacterial Outer Membrane Permeability Revisited", Microbiology and Molecular Biology Reviews, Dec. 2003, vol. 67, No. 4, pp. 593-656.

Osborn, M.J. et al. "Mechanism of Assembly of the Outer Membrane of *Salmonella typhimurium*: Isolation and Chracterization of Cytoplasmic and Outer Membrane", The Journal of Biological Chemistry, Jun. 25, 1972, vol. 247, No. 12, pp. 3962-3972.

Paradis-Bleau, C. et al. "A Genome-Wide Screen for Bacterial Envelope Biogenesis Mutants Identifies a Novel Factor Involved in Cell Wall Precursor Metabolism", PLOS Genetics, Jan. 2014, vol. 10, Iss. 1, e. 1004056.

Paradis-Bleau, C. et al. "Lipoprotein Cofactors Located in the Outer Membrane Activate Bacterial Cell Wall Polymerases", Cell, Dec. 23, 2010, vol. 143, pp. 1110-1120.

Perez, J. et al. "Functional Analysis of the Large Periplasmic Loop of the *Escherichia coli* K-12 WaaL O-Antigen Ligase", Molecular Microbiology (2008) vol. 70, No. 6, pp. 1424-1440.

Perkins, H.R., "Specifity of Combination between Mucopeptide Precursors and Vancomycin or Ristocetin", The Biochemical Journal, (1969) vol. 111, pp. 195-205.

Prats, R. & Pedro, M. "Normal Growth and Division of *Escherichia coli* with a reduced amount of Murein", Journal of Bacteriology, Jul. 1989, vol. 171, No. 7, pp. 3740-3745.

Raetz, C. & Whitfield, C., "Lipopolysaccharide Endotoxins", Annual Review of Biochemistry. (2002), pp. 635-700.

Ricci, D. & Silhavy, T., "The Barn Machine: A Molecular Cooper", Biochimica et Biophysica Acta (2012) vol. 1818, pp. 1067-1084.

Rigel, N. et al., "BamE Modulates the *Escherichia coli* Beta-Barrel Assembly Machine Component BarnA", Journal of Bacteriology Mar. 2012, vol. 194, No. 5, pp. 1002-1008.

Ruan, X. et al. "The WaaL O-Antigen Lipoloysaccharide Ligase has Features in Common with Meal Ion-Independent Inverting Glycosyltransferases", Glycobiology (2012) vol. 22, No. 2, pp. 288-299.

Ruiz, N. et al. "Chemical Conditionality: A Genetic Strategy to Probe Organelle Assembly", Cell, Apr. 22, 2005, vol. 121, pp. 307-317.

Ruiz, N. et al. "Transport of Lipopolysaccharide Across the Cell Envelope: The Long Road of Discovery", Nature Reviews Microbiology, Sep. 2009, vol. 7, pp. 677-683.

Ruiz, N., "Bioinformatics Identification of MurJ (MviN) as teh Peptidoglycan Lipid II Flippase in *Escherichia coli*", Proceedings of the Natural Academy of Sciences, Oct. 7, 2008, vol. 105, No. 40, pp. 15553-15557.

(56) References Cited

PUBLICATIONS

Schmidt, G. et al. "Role of a Lipopolysaccharide Gene for Immunogenicity of the Enterobacterial Common Antigen", Journal of Bacteriology, May 1976, vol. 126, No. 2, pp. 579-586.

Sham, L., "MurJ is the Flippase of Lipid-Linked Precursors for Petidoglycan Biogenesis", Science, Jul. 11, 2014, vol. 345, Iss. 6193, pp. 220-222.

Sieradzki, K. & Tomasz, A. "Inhibition or Cell Wall Turnover and Autolysis by Vancomycin in a Highly Vancomycin-Resistant Mutant of *Staphylococcus aureus*", Journal of Bacteriology, Apr. 1997, vol. 179, No. 8, pp. 2557-2566.

Singer, M. et al. "A Collection of Stains Containing Genetically Linked Alternating Antibiotic Resistance Elements for Genetic Mapping of *Escherichia coli*", Microbiological Reviews, Mar. 1989, vol. 53, No. 1, pp. 1-24.

Sklar, J. et al. "Lipoprotein SmpA is a Component of the YaeT Complex that Assembles Outer Membrance Proteins in *Escherichia coli*", Proceedings of the Natural Academy of Sciences, Apr. 10, 2007, vol. 104, No. 15, pp. 6400-6405.

SEQUENCE LISTING

```
<160> NUMBER OF SEQ ID NOS: 2

<210> SEQ ID NO 1
<211> LENGTH: 419
<212> TYPE: PRT
<213> ORGANISM: Escherichia coli

<400> SEQUENCE: 1

Met Leu Thr Ser Phe Lys Leu His Ser Leu Lys Pro Tyr Thr Leu Lys
1               5                   10                  15

Ser Ser Met Ile Leu Glu Ile Ile Thr Tyr Ile Leu Cys Phe Phe Ser
            20                  25                  30

Met Ile Ile Ala Phe Val Asp Asn Thr Phe Ser Ile Lys Ile Tyr Asn
        35                  40                  45

Ile Thr Ala Ile Val Cys Leu Leu Ser Leu Ile Leu Arg Gly Arg Gln
    50                  55                  60

Glu Asn Tyr Asn Ile Lys Asn Leu Ile Leu Pro Leu Ser Ile Phe Leu
65                  70                  75                  80

Ile Gly Leu Leu Asp Leu Ile Trp Tyr Ser Ala Phe Lys Val Asp Asn
                85                  90                  95

Ser Pro Phe Arg Ala Thr Tyr His Ser Tyr Leu Asn Thr Ala Lys Ile
            100                 105                 110

Phe Ile Phe Gly Ser Phe Ile Val Phe Leu Thr Leu Thr Ser Gln Leu
        115                 120                 125

Lys Ser Lys Lys Glu Ser Val Leu Tyr Thr Leu Tyr Ser Leu Ser Phe
    130                 135                 140

Leu Ile Ala Gly Tyr Ala Met Tyr Ile Asn Ser Ile His Glu Asn Asp
145                 150                 155                 160

Arg Ile Ser Phe Gly Val Gly Thr Ala Thr Gly Ala Ala Tyr Ser Thr
                165                 170                 175

Met Leu Ile Gly Ile Val Ser Gly Val Ala Ile Leu Tyr Thr Lys Lys
            180                 185                 190

Asn His Pro Phe Leu Phe Leu Leu Asn Ser Cys Ala Val Leu Tyr Val
        195                 200                 205

Leu Ala Leu Thr Gln Thr Arg Ala Thr Leu Leu Leu Phe Pro Ile Ile
    210                 215                 220

Cys Val Ala Ala Leu Ile Ala Tyr Tyr Asn Lys Ser Pro Lys Lys Phe
225                 230                 235                 240

Thr Ser Ser Ile Val Leu Leu Ile Ala Ile Leu Ala Ser Ile Val Ile
                245                 250                 255

Ile Phe Asn Lys Pro Ile Gln Asn Arg Tyr Asn Glu Ala Leu Asn Asp
            260                 265                 270

Leu Asn Ser Tyr Thr Asn Ala Asn Ser Val Thr Ser Leu Gly Ala Arg
        275                 280                 285

Leu Ala Met Tyr Glu Ile Gly Leu Asn Ile Phe Ile Lys Ser Pro Phe
    290                 295                 300
```

```
Ser Phe Arg Ser Ala Glu Ser Arg Ala Glu Ser Met Asn Leu Leu Val
305                 310                 315                 320

Ala Glu His Asn Arg Leu Arg Gly Ala Leu Glu Ser Ser Asn Val His
            325                 330                 335

Leu His Asn Glu Ile Ile Glu Ala Gly Ser Leu Lys Gly Leu Met Gly
            340                 345                 350

Ile Phe Ser Thr Leu Phe Leu Tyr Phe Ser Leu Phe Tyr Ile Ala Tyr
            355                 360                 365

Lys Lys Arg Ala Leu Gly Leu Leu Ile Leu Thr Leu Gly Ile Val Gly
        370                 375                 380

Ile Gly Leu Ser Asp Val Ile Ile Trp Ala Arg Ser Ile Pro Ile Ile
385                 390                 395                 400

Ile Ile Ser Ala Ile Val Leu Leu Val Ile Asn Asn Arg Asn Asn
                405                 410                 415

Thr Ile Asn

<210> SEQ ID NO 2
<211> LENGTH: 419
<212> TYPE: PRT
<213> ORGANISM: Escherichia coli

<400> SEQUENCE: 2

Met Leu Thr Ser Phe Lys Leu His Ser Leu Lys Pro Tyr Thr Leu Lys
1               5                   10                  15

Ser Ser Met Ile Leu Glu Ile Ile Thr Tyr Ile Leu Cys Phe Phe Ser
            20                  25                  30

Met Ile Ile Ala Phe Val Asp Asn Thr Phe Ser Ile Lys Ile Tyr Asn
        35                  40                  45

Ile Thr Ala Ile Val Cys Leu Leu Ser Leu Ile Leu Arg Gly Arg Gln
    50                  55                  60

Glu Asn Tyr Asn Ile Lys Asn Leu Ile Leu Pro Leu Ser Ile Phe Leu
65                  70                  75                  80

Ile Gly Leu Leu Asp Leu Ile Trp Tyr Ser Ala Phe Lys Val Asp Asn
                85                  90                  95

Ser Pro Phe Arg Ala Thr Tyr His Ser Tyr Leu Asn Thr Ala Lys Ile
            100                 105                 110

Phe Ile Phe Gly Ser Phe Ile Val Phe Leu Thr Leu Thr Ser Gln Leu
        115                 120                 125

Lys Ser Lys Lys Glu Ser Val Leu Tyr Thr Leu Tyr Ser Leu Ser Phe
    130                 135                 140

Leu Ile Ala Gly Tyr Ala Met Tyr Ile Asn Ser Ile His Glu Asn Asp
145                 150                 155                 160

Arg Ile Ser Phe Gly Val Gly Thr Ala Thr Gly Ala Ala Tyr Ser Thr
                165                 170                 175

Met Leu Ile Gly Ile Val Ser Gly Val Ala Ile Leu Tyr Thr Lys Lys
            180                 185                 190

Asn His Pro Phe Leu Phe Leu Leu Asn Ser Cys Ala Val Leu Tyr Val
        195                 200                 205

Leu Ala Leu Thr Gln Thr Arg Ala Thr Leu Leu Phe Pro Ile Ile
    210                 215                 220

Cys Val Ala Ala Leu Ile Ala Tyr Tyr Asn Lys Ser Pro Lys Lys Phe
225                 230                 235                 240

Thr Ser Ser Ile Val Leu Leu Ile Ala Ile Leu Ala Ser Ile Val Ile
                245                 250                 255
```

-continued

```
Ile Phe Asn Lys Pro Ile Gln Asn Arg Tyr Asn Glu Ala Leu Asn Asp
            260             265             270

Leu Asn Ser Tyr Thr Asn Ala Asn Ser Val Thr Ser Leu Gly Ala Arg
        275             280             285

Leu Ala Met Tyr Glu Ile Gly Leu Asn Ile Phe Ile Lys Ser Pro Phe
    290             295             300

Ser Phe Arg Ser Ala Glu Ser Arg Ala Glu Ser Met Asn Leu Leu Val
305             310             315             320

Ala Glu His Asn Arg Leu Arg Gly Ala Leu Glu Phe Ser Asn Val His
            325             330             335

Leu His Asn Glu Ile Ile Glu Ala Gly Ser Leu Lys Gly Leu Met Gly
            340             345             350

Ile Phe Ser Thr Leu Phe Leu Tyr Phe Ser Leu Phe Tyr Ile Ala Tyr
        355             360             365

Lys Lys Arg Ala Leu Gly Leu Leu Ile Leu Thr Leu Gly Ile Val Gly
    370             375             380

Ile Gly Leu Ser Asp Val Ile Ile Trp Ala Arg Ser Ile Pro Ile Ile
385             390             395             400

Ile Ile Ser Ala Ile Val Leu Leu Leu Val Ile Asn Asn Arg Asn Asn
            405             410             415

Thr Ile Asn
```

MODIFIED LIPOPOLYSACCHARIDE GLYCOFORM AND METHOD OF USE

CROSS-REFERENCE TO PRIOR FILED APPLICATIONS

This application is a divisional application of U.S. patent application Ser. No. 14/707,718, filed May 8, 2015. This application also claims the benefit of U.S. Provisional Application No. 61/991,116, filed May 9, 2014, and U.S. Provisional Application No. 62/098,014, filed Dec. 30, 2014, which are incorporated herein in their entirety.

STATEMENT REGARDING FEDERALLY SPONSORED RESEARCH OR DEVELOPMENT

This invention was made with government support under Grant No. GM034821 awarded by the National Institutes of Health and Grant No. AI081059 awarded by the National Institutes of Health. The government has certain rights in this invention.

BACKGROUND OF THE INVENTION

A peptidoglycan (PG) cell wall is an essential extracytoplasmic feature of most bacteria (Singer et al., 1989); this essentiality has made its biogenesis a fruitful target for antibiotics, including vancomycin and penicillin. The cell wall is directly exposed to the extracellular milieu in Gram-positive bacteria, but is shielded in *Escherichia coli* (*E. coli*) and other Gram-negative species by a highly selective permeability barrier formed by the outer membrane (OM). The OM prevents influx of antibiotics, such as vancomycin, restricting their access to intracellular targets (Eggert et al., 2001; Ruiz et al., 2005).

Lipopolysaccharide (LPS) forms the surface-exposed outer leaflet of the OM and is key to the barrier function (Osborn et al., 1972; Kamio and Nikaido, 1976; Nikaido, 2003). LPS is a glycolipid consisting of a 'lipid A' anchor within the bilayer, and a set of covalently attached distal 'core' saccharides (Raetz and Whitfield, 2002). LPS is made at the cytosolic leaflet of the inner membrane (IM) before being flipped to the periplasmic leaflet (Zhou et al., 1998). A transenvelope complex of seven lipopolysaccharide transport proteins (LptABCDEFG) delivers LPS from the IM to the OM (Ruiz et al., 2009; Chng, Gronenberg, et al., 2010). A sub-complex of the β-barrel LptD and lipoprotein LptE resides within the OM and accomplishes the final step of inserting LPS into the outer leaflet (Chng, Ruiz, et al., 2010).

LPS and PG are both potent activators of immune responses via distinct stimulatory mechanisms. However, LPS is inherently toxic to humans and animals due to hyper-activation of inflammatory immune responses. Detoxification can eliminate some or all of the endotoxicity, but the less toxic variants generally also have reduced immunostimulatory properties. LPS-stimulated immune responses can be synergistically increased by co-stimulation with PG added into a mixture (Fritz et al., 2005). Therefore, this synergy is likely to be improved by direct coupling of LPS and PG into a single molecule that allows both activators to stimulate their associated pathways. A detoxified LPS-PG molecule will likely retain more desirable immunostimulatory properties in comparison to detoxified LPS alone.

BRIEF SUMMARY OF THE INVENTION

Mutant O-antigen ligases are disclosed. It includes isolated proteins that have the amino acid sequence SEQ ID NO: 1, or isolated proteins having at least 90% sequence identity to SEQ ID NO: 2 and having an amino acid substitution of phenylalanine to serine at the phenylalanine homologous to position 332 of SEQ ID NO: 2. A vaccine adjuvant may also be produced from a lipopolysaccharide or a lipopolysaccharide derivative isolated from a mutant O-antigen ligase. A polynucleotide may also encode a mutant O-antigen ligase.

A LPS glycoform modified with peptidoglycan cell wall fragments is also disclosed. The LPS glycoform may be adapted to display antibiotic-specific binding sites at a cell surface, of which vancomycin is one such antibiotic. The LPS glycoform may be able to activate receptors or signaling pathways within the human body, including TRL4/MD2 NOD1, and NOD2 receptors, and the TRIF/TRAM pathways.

A bacterium that expresses a LPS glycoform is also disclosed. The bacterium may include a gene encoding a mutant O-antigen ligase.

A method for creating an LPS molecule is also disclosed. An *E. coli* strain is provided that expresses a mutant O-antigen ligase, it is placed in conditions allowing it to grow, and then the LPS molecule is isolated. The LPS molecule may be isolated by separating the molecules based on at least one of the group consisting of size, chemical composition, and affinity for a particular binding agent.

A method for generating a LPS* derivative molecule is also disclosed. An *E. coli* strain is provided that expresses a LPS derivative molecule having reduced endotoxicity, modifying the *E. coli* strain by creating a mutant O-antigen ligase, and placing it in conditions allowing it to grow and produce the LPS* molecule. The LPS* derivative molecule may be isolated at that time. The LPS derivative molecule may be 3-O-deacyl-4'-monophosphoryl lipid A. A vaccine adjuvant may also be created, comprising the LPS* derivative molecule.

A modified LPS molecule having at least one non-native sugar and a greater molecular weight as compared to the LPS molecule it is modified from is also disclosed.

DETAILED DESCRIPTION OF THE INVENTION

The present disclosure generally relates to the genetic engineering of bacteria. More particularly, the present disclosure relates to genetic engineering of a gram-negative bacteria expressing a modified LPS molecule, and methods for making and using the molecule.

While the present disclosure is susceptible to various modifications and alternative forms, specific example embodiments are herein described in more detail. It should be understood, however, that the description of specific example embodiments is not intended to limit the invention to the particular forms disclosed. The features and advantages of the present invention will be apparent to those skilled in the art. While numerous changes may be made by those skilled in the art, such changes are within the spirit of the invention.

A recently described lptE mutation (lptE613) causes defective LPS transport and leads to increased antibiotic sensitivity (Malojčić et al., 2014). In certain aspects of the invention, an isolated vancomycin-resistant strain of *E. coli* carrying a F332S substitution in the O-antigen ligase gene (waaL) and capable of restoring vancomycin resistance was isolated and characterized (See FIG. 1).

Figure 1:
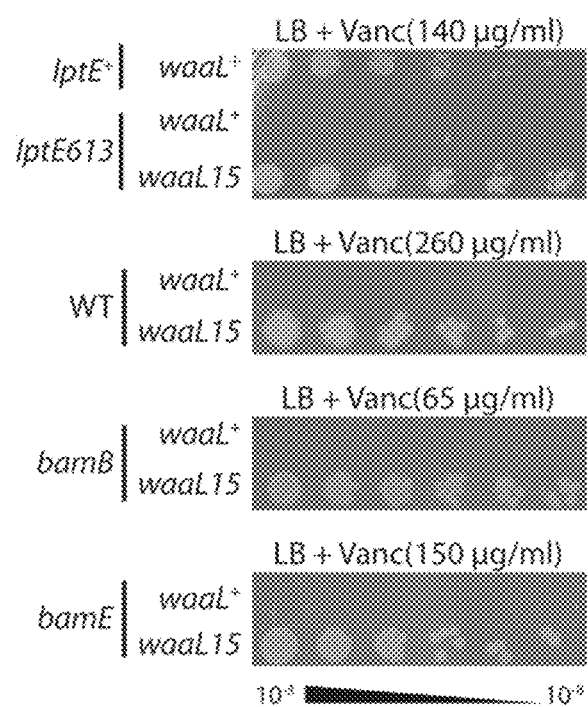
FIG. 1 shows analysis of various strains utilizing one aspect of the invention with regards to vancomycin resistance.
Figure 2:
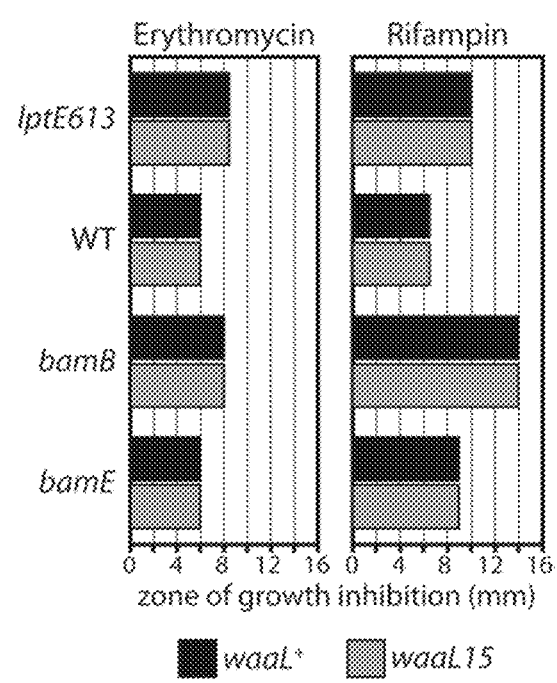
FIG. 2 shows analysis of one aspect of the invention with regards to resistance to two alternate antibiotics.

One embodiment of this invention increases vancomycin resistance in strains carrying bamB or bamE null mutations that disrupt the OM barrier by causing defects in β-barrel protein assembly (See FIG. 1). Certain embodiments of the invention also increase vancomycin-resistance across different strains, including the wild-type strain (See FIG. 1).

Figure 3:
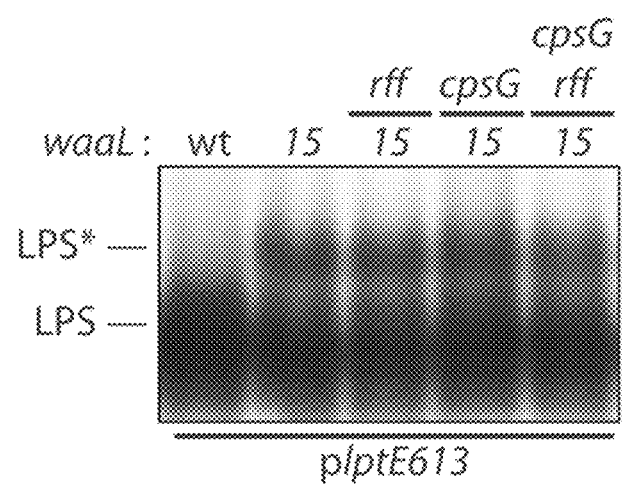
FIGS. 3-4 shows the SDS-PAGE analysis of LPS molecules from various strains.

The domesticated *E. coli* K-12 does not produce the normal substrate (O—Ag) of waaL (Liu and Reeves, 1994) and a waaL deletion does not suppress vancomycin sensitivity, indicating that waaL15 is a gain of function mutation. Thus, certain aspects of the embodied invention must have an altered activity. Silver-staining of isolated LPS confirmed that waaL15 modifies LPS with additional sugars to produce one embodiment of this invention, a novel glycoform (LPS* herein), detected as a higher molecular weight band that is absent in waaL+ (See FIG. 3).

Figure 4:
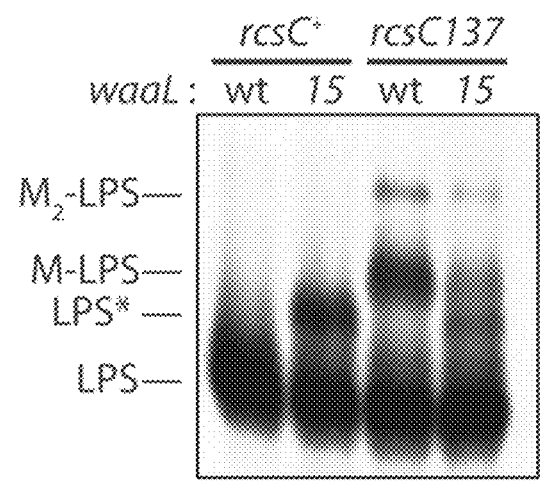
Figure 5:
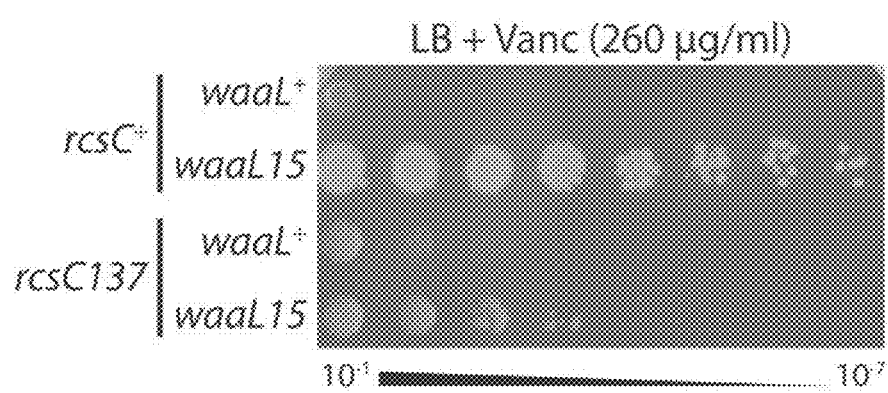
FIG. 5 shows analysis of various strains utilizing one aspect of the invention with regards to vancomycin resistance.

WaaL can use two minor saccharide substrates to modify LPS in *E. coli* K-12: enterobacterial common-antigen (ECA) and colanic acid (CA). ECA-modified LPS is a minor constituent of the OM (Schmidt et al., 1976; Meredith et al., 2007). Production of CA is regulated by the Rcs phosphorelay stress response system, and CA-modified LPS (called 'M-LPS') is only detectable during severe envelope stress (Meredith et al., 2007). LPS silver-staining revealed that LPS* remained detectable following inactivation of biosynthesis of ECA (rff), CA (cpsG), or both these polysaccharides (rff cpsG) (See FIG. 3). Increasing the amounts of a competing substrate by introducing the rcsC137 mutation to activate expression of the genes for CA biosynthesis (Gottesman et al., 1985), lowered LPS* abundance at the expense of increased M-LPS (See FIG. 4). The decrease in LPS* correlated with a significant reduction in vancomycin-resistance, indicating that LPS* molecules directly mediate the resistance (FIG. 5). WaaL15 is able to use a new substrate and thereby generate a previously uncharacterized LPS glycoform that provides a specific mechanism for vancomycin resistance.

Figure 6:
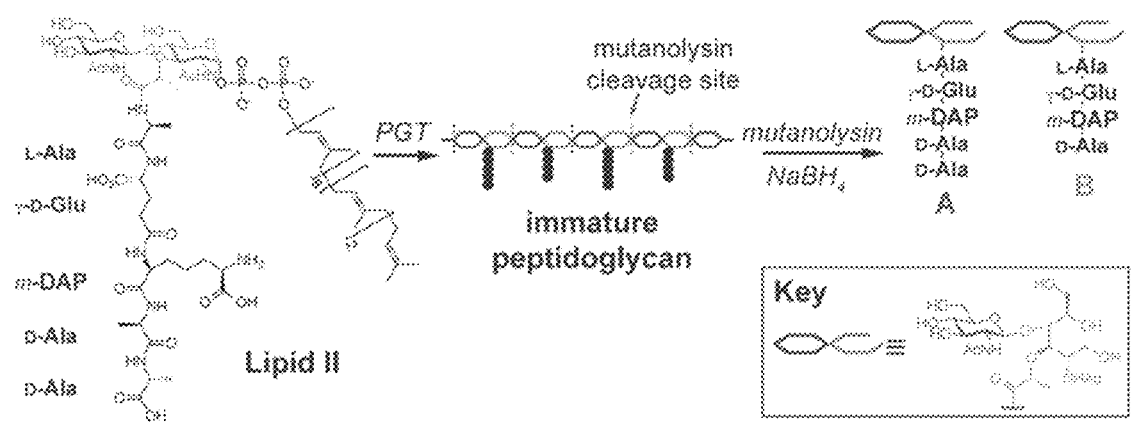
FIG. 6 shows the structure of Lipid II and schematic of peptidoglycan cleavage by mutanolysin that releases pentapeptide ("A") and tetrapeptide ("B") species.
Figure 7:
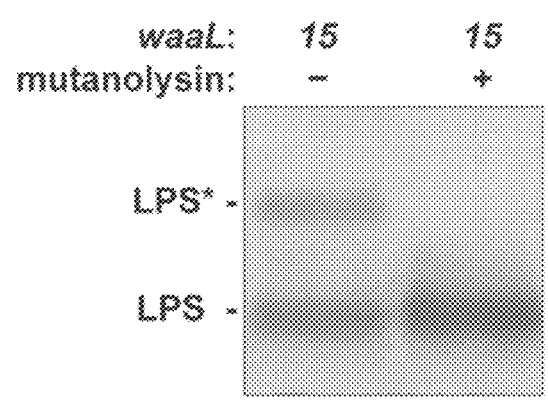
FIG. 7 shows analysis indicating waaL15 isolate LPS treated with mutanolysin cleaves the LPS* modification.

All native WaaL substrates contain carbohydrates linked to a common undecaprenyl (Und) lipid carrier. PG biosynthesis involves a disaccharide pentapeptide (DPP) linked to the same Und carrier, a molecule called lipid II (See FIG. 6). Isolated LPS* was treated with the muralytic enzyme mutanolysin (See FIGS. 6 and 7). Digestion of purified LPS*, but not LPS, liberated near-stoichiometric quantities of fragments that were identified by mass spectrometry as DPP or derivatives with a tetrapeptide stem (See FIG. 8). There was no evidence for cross-linked products suggesting that lipid II was the source of the LPS* glycosylation.

Figure 8:
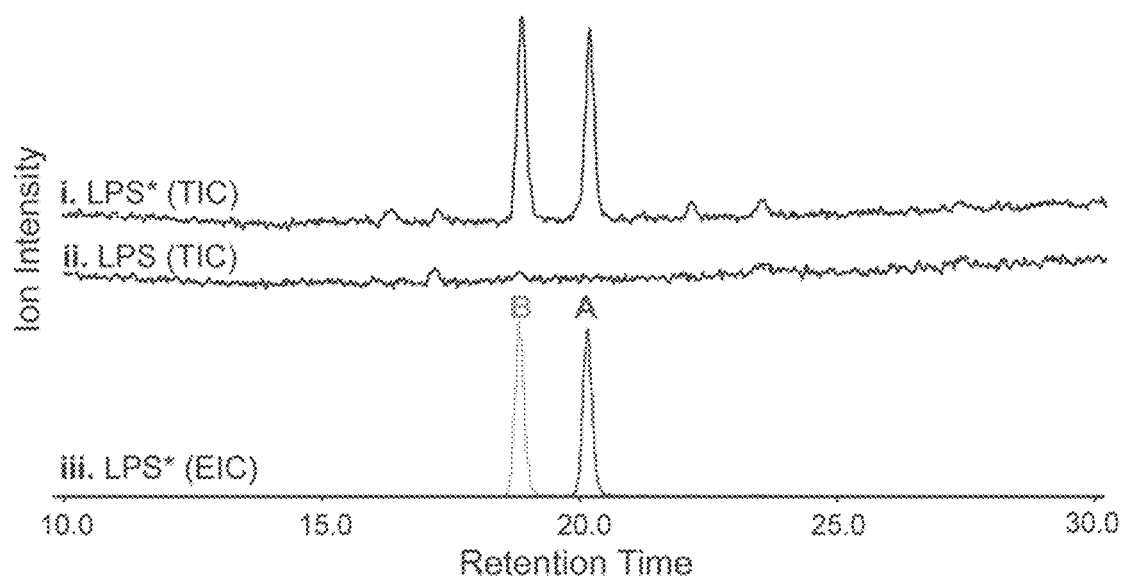
FIG. 8 shows total ion chromatograms for degradation products of LPS and LPS*, and a total ion chromatogram for LPS* degradation.
Figure 9:
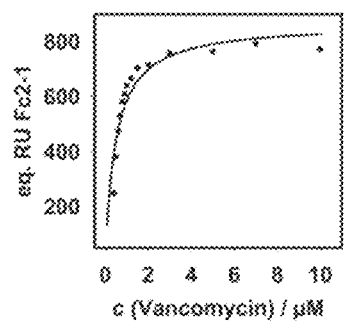
FIG. 9 shows the equilibrium signal of the reference subtracted SPR binding kinetics at 25° C.
Figure 10:
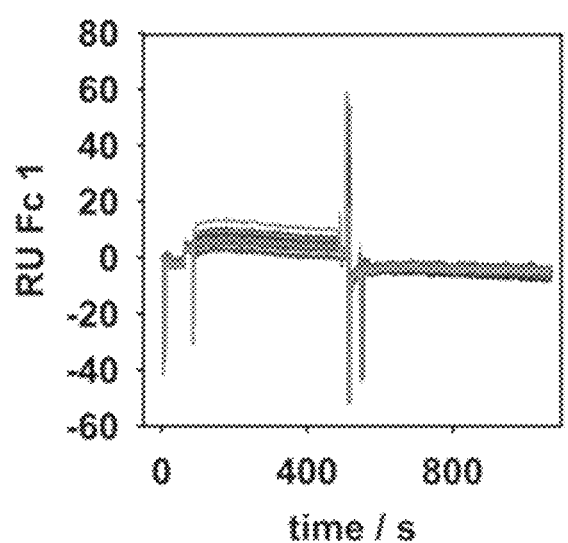
FIG. 10 shows the SPR binding kinetics at 25° C. of various concentrations of vancomycin passing over surfaces of total isolated LPS from waaL+.
Figure 11:
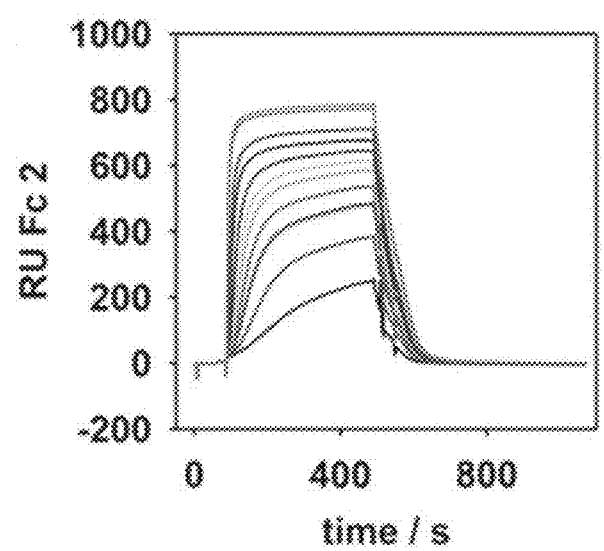
FIG. 11 shows the SPR binding kinetics at 25° C. of various concentrations of vancomycin passing over surfaces of total isolated LPS from waaL15.
Figure 12:
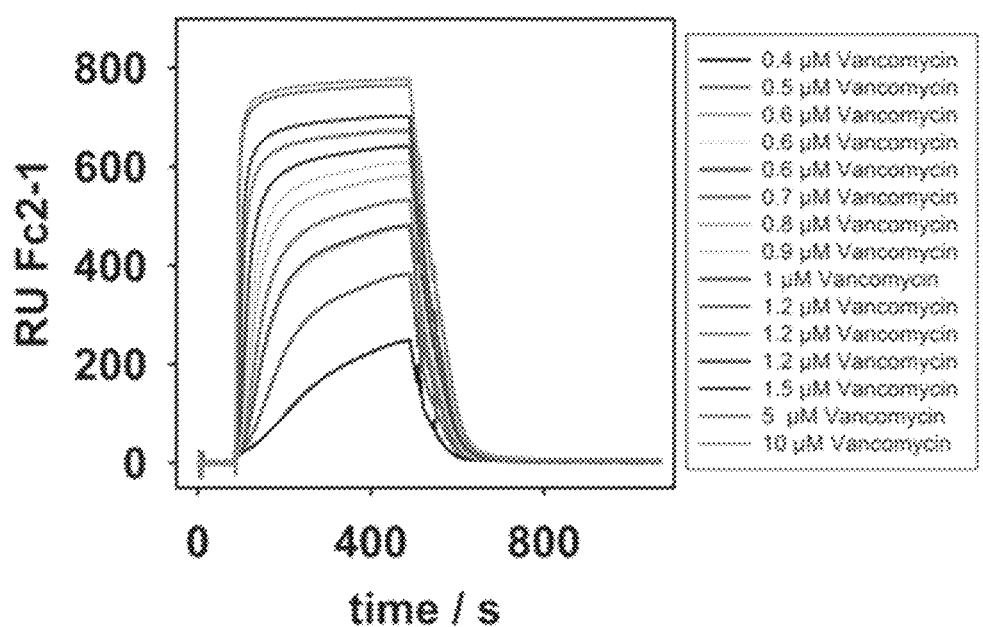
FIG. 12 shows the reference subtracted SPR binding kinetics at 25° C.

There are several carboxypeptidases in the periplasm that remove the terminal D-Alanine (D-Ala) from DPP to produce the tetrapeptide derivative. Indeed, *E. coli* PG contains negligible amounts of pentapeptide stems. FIG. 8 shows that, in at least one instance, about 50% of the LPS* is sequestered before it can be attacked by one of these carboxypeptidases. It is expected that sequestration occurs because the molecule is transported from the periplasm to the cell surface.

Peptide stems from adjacent peptidoglycan strands in the cell wall are cross-linked via transpeptidation between the penultimate D-Ala on one stem and a meso-diaminopimelic acid(m-DAP) residue on a nearby stem (Vollmer et al., 2008). Extensive cross-linking produces a rigid macromolecular meshwork that is vital to cell wall function. Vancomycin binds and sequesters the terminal D-Ala-D-Ala residues of a pentapeptide stem in order to inhibit transpeptidation (Perkins, 1969). Since LPS* was the product of DPP ligation onto LPS, this modified glycoform should contain vancomycin binding sites.

Several vancomycin-resistance mechanisms exist in Gram-positive bacteria, including: alterations in peptidoglycan metabolism can produce thicker cell walls (Cui et al., 2003); and transpeptidation can be reduced to leave more free D-Ala-D-Ala residues within the established cell wall structure (Sieradzki and Tomasz, 1997). In one aspect of the invention, it has been shown that the waaL15 mechanism is comparable since it also increases the number of free D-Ala-D-Ala targets that can tie up vancomycin. Moreover, by displaying D-Ala-D-Ala at the cell surface the waaL15 mutation titrates vancomycin away from the true drug target, in an altogether different cellular compartment. Therefore, certain embodiments of the invention confer resistance by acting as a molecular decoy for vancomycin.

It should be understood by those skilled in the art that in certain other embodiments, the present disclosure may provide improved delivery of vaccines or improved vaccine adjuvants derived from the LPS* molecule of the present invention.

The biosynthesis of LPS* is remarkable. Lipid II in *E. coli* is extremely scarce, its steady-state abundance is thought to be only 1,000-2,000 molecules per cell (van Heijenoort et al., 1992). Insertion of new PG is thought to occur via large multiprotein morphogenic complexes: the elongasome and the divisome, responsible for PG synthesis along the lateral cell body and at the septum, respectively. In order to overcome the scarcity of lipid II and limit its diffusion away from sites of PG growth, both complexes are suggested to include at least some of the lipid II biosynthetic enzymes, and the presumed flippases that deliver lipid II from the site of synthesis in the cytoplasm to the site of cell wall assembly in the periplasm (Szwedziak and Lowe, 2013). In this model, the substrate for PG synthesis would be isolated physically from the LPS assembly pathway. LPS is inserted into the OM of each cell at a rate exceeding 70,000 molecules per minute (Lima et al., 2013). It is estimated that approximately one-third of LPS is modified by WaaL15 with lipid II-sourced DPP. Clearly, WaaL15 has ready access to lipid II and this is inconsistent with a model of diffusion-limited lipid II sequestered at the elongasome or divisome complexes. Recent evidence also points to wider lipid II availability (Lee et al., 2014; Sham et al., 2014). The recharging of the lipid carrier with new DPP must also be extremely efficient to maintain such a robust pool of PG precursor.

WaaL15 drains the available lipid II pool with no apparent detriment to cell wall integrity. Lipid II limitation can be revealed by synthetic genetic interactions in a strain lacking the elongasome (Paradis-Bleau et al., 2014), but it is not the recharging of lipid II that is limiting, rather it is the biosynthesis of DPP. Table 1 lists some synthetic interactions between waaL15 and mutations affecting the elongasome due to limited lipid II availability.

production of LPS*, the *Escherichia coli* waaL15 mutant bacteria typically produce both native LPS and the LPS* glycoform. Consequently, established "total LPS extraction" methods that have been performed on cultures of these bacteria yield a mixture of LPS and LPS*. While this may be sufficient for some purposes, it is expected that other purification methods, or a combination of methods, may provide improved isolation and purification of the LPS* component Other methods beyond "total LPS extraction" methods envisioned as part of this method include, but are not limited to, size-based chromatography that exploits LPS*'s increased size and altered chemical composition compared to LPS, or affinity-based methods that exploit the specific binding of LPS* to vancomycin.

The use of LPS as an adjuvant is precluded by strong endotoxicity. LPS derivates isolated following acid and base hydrolysis have significantly reduced endotoxicity but remain immunostimulatory. One such LPS derivative is 3-O-deacyl-4'-monophosphoryl lipid A (MPL, GSK) which

TABLE 1

| Relevant Genes* | | | Cotransduction | |
| --- | --- | --- | --- | --- |
| Donor | Recipient | Selected Allele | Gene | Frequency |
| yhfT3084::Tn10 mrcA::kan | waaL+ | yhfT-3084::Tn10 | mrcA::kan | 85% |
| yhfT3084::Tn10 mrcA::kan | waaL15 | yhfT-3084::Tn10 | mrcA::kan | 89% |
| sfsB203::Tn10 lpoA::kan | waaL+ | sfsB203::Tn10 | lpoA::kan | 29% |
| sfsB203::Tn10 lpoA::kan | waaL15 | sfsB203::Tn10 | lpoA::kan | 28% |
| zad-220::Tn10 mrcB::kan | waaL+ | zad-220::Tn10 | mrcB::kan | 72% |
| zad-220::Tn10 mrcB::kan | waaL15 | zad-220::Tn10 | mrcB::kan | 13% |
| zce-726::Tn10 lpoB::kan | waaL+ | zce-726::Tn10 | lpoB::kan | 77% |
| zce-726::Tn10 lpoB::kan pMurA† | waaL15 | zce-726::Tn10 | lpoB::kan | 5% |
| zad-220::Tn10 mrcB::kan | waaL+ | zad-220::Tn10 | mrcB::kan | 79% |
| zad-220::Tn10 mrcB::kan | waaL15 | zad-220::Tn10 | mrcB::kan | 77% |
| zce-726::Tn10 lpoB::kan | waaL+ | zce-726::Tn10 | lpoB::kan | 75% |
| zce-726::Tn10 lpoB::kan | waaL15 | zce-726::Tn10 | lpoB::kan | 70% |

*mrcA encodes PBP1A which functions with LpoA in the divisome; mrcB encodes PBP1B which functions with LpoB in the elongasome.
†Expression of murA was induced by supplementing growth media with 100 µM IPTG.

In many bacteria, LPS is decorated with highly variable O-Ags that are linear polymers of repeating units of 3-6 monosaccharides (Kalynych et al., 2014). In *E. coli* the multitude of different O-Ags initiate with GlcNAc, ECA also initiates with GlcNAc. In *E. coli* K-12 when colonic acid is overproduced M-LPS is made from an initiating Glc residue. The F332S mutation broadens substrate specificity of the WaaL glycosyltransferase allowing it to efficiently accept a significantly more bulky initiating MurNAc with an attached oligopeptide stem. The only other glycosyltransferase that is known to use lipid II as a substrate is PglL from Neisseria and the use required overproduction of the enzyme in *E. coli* (Faridmoayer et al., 2008). It is also remarkable that no OM biogenesis defect in strains carrying waaL15 is detected, demonstrating that the Lpt system is fully competent for the transport and assembly of LPS* despite the addition of both unnatural sugars and peptide stems. Both LPS and PG are pathogen-associated molecular patterns (PAMPs) that potently activate innate immune responses via distinct pathways, and it seems sensible for Gram-negative bacteria to keep these entities separated. It is expected that the F332S substitution has inactivated an exclusion mechanism that prevents WaaL from utilizing the lipid II pool.

In certain embodiments of the invention, the present disclosure provides for bacteria modified with the waaL15 mutation, or a bacterium modified to express LPS*. During is part of the adjuvant formulation AS04 used in the Cervarix™ human papillomavirus vaccine (GSK). LPS* molecules are likely sensitive to acid and base hydrolysis. It is known in the art that strains of *E. coli* may be engineered to produce LPS derivatives without the need a harsh chemical treatment that would likely be incompatible with LPS*. It is therefore expected that introducing the waaL15 mutation into LPS derivative producing strains, such as those producing 3-O-deacyl-4'-monophosphoryl lipid A, will produce a detoxified LPS* derivative that retains at least some of the immunogenic properties of LPS*.

Certain embodiments of the invention provide for producing a modified lipopolysaccharide molecule that enables the molecule to activate at least some of the immune signaling receptors and pathways of traditional LPS and PG, including TLR4, MD2, NOD1, and NOD2 receptors, and TRIF/TRAM pathways. It is expected that applying LPS* treatment to human TLR4/MD2, NOD1, and NOD2 reporter cell lines will confirm signaling through this receptor and downstream pathway, and that LPS*-treated human cell lines will show activation via the TRIF/TRAM pathway using transcriptomic analysis.

To facilitate a better understanding of the present invention, the following examples of certain aspects of some embodiments are given. In no way should the following examples be read to limit, or define, the entire scope of the invention.

EXAMPLES

Construction of Mutant Strains

Strains and plasmids used in this study are listed in Table 2 and Table 3, respectively. Strains were grown in lysogeny broth (LB, Miller) or M63 minimal medium under aeration at 37° C. unless otherwise noted. When appropriate, media were supplemented with kanamycin (Kan, 25 µg/ml), ampicillin (Amp, 25-125 µg/ml), tetracycline (Tet, 20 µg/ml), chloramphenicol (Cam, 20 µg/ml), vancomycin (Vanc, 65-260 µg/ml) and arabinose (Ara, 0.2% v/v).

Kanamycin deletion-insertion mutations of bamE, cpsG, mrcA, mrcB, lpoA and lpoB were obtained from the Keio collection (Baba et at, 2006). ECA null rff::Tn10-66 allele was obtained from strain 21566 (Meier-Dieter et al., 1990). The ompC::Tn5 rcsC137 was obtained from strain SG20803 (Brill et at, 1988). Mutant alleles were introduced by P1vir transduction.

TABLE 2

| Strain | Relevant Genotype | Reference |
|---|---|---|
| MC4100 | F⁻ araD139 I⁻ (arg-lac)U169 rpsL150 relA1 flbB5301 deoC1 ptsF25 thi | (Casadaban, 1976) |
| NR754 | MC4100 Ara⁺ | (Button et al., 2007) |
| CAG12025 | F⁻ araD139 I⁻ rph-1 zad-220::Tn10 | (Singer et al., 1989) |
| CAG12072 | F⁻ araD139 I⁻ rph-1 sfsB203::Tn10 | (Singer et al., 1989) |
| CAG12078 | F⁻ araD139 I⁻ rph-1 zce-726::Tn10 | (Singer et al., 1989) |
| CAG18456 | F⁻ araD139 I⁻ rph-1 yhfT3084::Tn10 | (Singer et al., 1989) |
| MG617 | NR754 ΔlptE2::kan/plptE⁺ | (Malojčić et al., 2014) |
| MG1029 | NR754 ΔlptE2::kan/plptE613 | (Malojčić et al., 2014) |
| MG1088 | NR754 ΔlptE2::kan waaL15/plptE613 | This study |
| MG1167 | NR754 ΔlptE2 waaL15/plptE613 | This study |
| MG1180 | MG1167 ΔcpsG::kan | This study |
| MG1181 | MG1210 ΔbamE::kan | This study |
| MG1182 | MG1211 ΔbamE::kan | This study |
| MG1196 | MG1210 bamB::kan | This study |
| MG1197 | MG1211 bamB::kan | This study |
| MG1210 | NR754 waaL⁺ tdh::Tn10 | This study |
| MG1211 | NR754 waaL15 tdh::Tn10 | This study |
| MG1214 | MG1167 ΔcpsG::kan rff::Tn10 | This study |
| MG1234 | MG1167 rff::Tn10-66 | This study |
| MG1378 | MG1210 ompC::Tn5::kan rcsC137 | This study |
| MG1379 | MG1211 ompC::Tn5 rcsC137 | This study |
| MG1642 | NR754 waaL⁺ | This study |
| MG1643 | NR754 waaL15 | This study |
| MG1635 | CAG12025 ΔmrcB::kan | This study |
| MG1636 | CAG18456 ΔmrcA::kan | This study |
| MG1671 | CAG12072 ΔlpoA::kan | This study |
| MG1672 | CAG12078 ΔlpoB::kan | This study |

TABLE 3

| Plasmid | Description | Reference |
|---|---|---|
| plptE | lptE cloned into pBAD18, Amp$^R$ | (Wu et al., 2006) |
| pMurA | ASKA plasmid with cloned murA, Cam$^R$ | (Kitagawa et al., 2006) |

Isolation and Identification of waaL15

Spontaneous suppressor mutants of strain MG1029 capable of growing on LB plates supplemented with vancomycin (140 µg/ml) were isolated; one such mutant strain was MG1088. The mutation locus conferring vancomycin-resistance in MG1088 was identified by linkage mapping using a library of random mini-Tn10 insertions (Kleckner et al., 1991). In this way, the tdh::Tn10 allele was found to be approximately 70% linked to the suppressor mutation waaL15. The F332S mutation was then identified by PCR amplification and sequencing of the waaL locus. The waaL15 mutation was moved into the NR754 wild-type strain by linkage with tdh::Tn10. In order to generate the unmarked waaL15 strain (MG1643) and its wild-type control (MG1642), the tdh::Tn10 mutation was removed from strains MG1210 and MG1211 by first introducing a linked ΔcysE::kan mutation (Baba et al., 2006), selecting for Kan$^R$ and screening for Tets transductants that were Vanc$^R$ (waaL15) or Vanc$^S$ (waaL⁺). The ΔcysE::kan mutation was then replaced with cysE⁺ by transduction, selection on M63 minimal medium, and screening of Vanc$^R$/Vanc$^S$.

Assessment of Genetic Linkage by Co-Transduction

The genetic interaction of PG synthase mutants with waaL15 was assessed as follows. Kan$^R$-marked null alleles of lpoA, lpoB, mrcA and mrcB were introduced by P1vir transduction into CAG strains that carry a Tn10 insertion in a nearby locus (see Table 1). Kan$^R$ Tet$^R$ transductants were isolated and used to generate P1vir lysates. These P1vir were used to transduce waaL⁺ (MG1642) or waaL15 (MG1643) strains, selecting for the Tn10 marker. The frequency with which the Kan$^R$-marked lpo and mrc alleles were co-transduced (genetically linked) was determined by replica plating on LB+Kan. Linkage was assessed in a total of 300 transductants from 3 independent experiments. A decrease in the cotransduction frequency in waaL15 strains relative to waaL indicates a synthetic interaction between waaL15 and the Kan$^R$-marked allele. The synthetic interaction between waaL15 and mrcB/lpoB null alleles was relieved in strains carrying pMurA when expression of the cloned murA gene (encoding the enzyme responsible for the first committed step in DPP biosynthesis) was induced with 100 µM isopropyl β-D-1-thiogalactopyranoside (IPTG). Overexpression of murA increases the cellular pool of UDP-MurNAc-pentapeptide and consequently also increases the pool of lipid II.

Analysis of LPS by SDS-PAGE and Silver Staining

A total to 1×10⁹ cells from liquid culture were taken, pelleted and resuspended 0.05 ml of 'LPS Sample Buffer' (0.66M Tris pH 7.6, 2% v/v sodium dodecyl sulfate [SDS], 10% v/vglycerol, 4% v/v β-mercaptoethanol, 0.1% w/v bromophenol blue). Samples were boiled for 10 min and allowed to cool to room temperature. 10 µl of Proteinase K (2.5 mg/ml, in LPS SampleBuffer) was added and samples were incubated at 56° C. for 16 h. LPS samples were then resolved by SDS-PAGE and silver stained as described previously (Tsai and Frasch, 1981). By quantifying band density using ImageJ, it was determined that LPS* constituted 29±1% of the total LPS in waaL15 samples.

Antibiotic Disc Diffusion Assay 3 ml of molten LB Top agar (0.75% agar) was inoculated with 0.1 ml of overnight culture. The mixture was poured onto a LB agar plate (1.5% agar,) and allowed to set. Antibiotic discs (BD Sensi-Disc) were placed on the Top agar overlay and plates were incubated overnight at 37° C. The 'zone of growth inhibition' was measured across the antibiotic disc.

Fluorescence Microscopy

Overnight cultures were sub-cultured at 1:100 into fresh LB broth and grown for 1.5 h. A1 ml aliquot was taken, pelleted and was twice washed with 1 ml M63 medium.

Cells were resuspended in 0.1 ml of M63 broth containing 1 μg/ml of vancomycin-BODIPY-FL (LifeTechnologies, V-34850). Cells were incubated at room temperature for 10 min and then washed twice with 1 ml M63 broth. Cells were then resuspended in 0.03 ml of M63 broth, and approximately 2 ml was spotted onto an M63-agarose pad. Cells were immediately visualized on a Nikon Eclipse 90i microscope with a Nikon Plan Apo 1.4/100× Oil Ph3 phase objective.

LPS Purification

E. coli MG1210 and MG1211 were each grown in 4×1.5 l LB medium shaking at 37° C. overnight to stationary phase. The cells were harvested by centrifugation for 15 min at 5,000×g, 4° C. and washed with water (700 ml) and ethanol (40 ml) once, then twice with acetone (40 ml). After drying the cell pellet in a desiccator overnight in vacuo, PCP (Phenol-Chloroform-petroleum ether) method was used for rough LPS extraction (Galanos et al., 1969).

PG Purification

E. coli MG1210 and MG1211 were each grown in 500 ml LB medium shaking at 37° C. to stationary phase (6 h). The cell wall was isolated from the culture as described by Glauner et al., (1988) and Uehara et al., (2009), with modifications described below. The cells were resuspended in 20 ml phosphate buffered saline (PB, pH=7.4) and boiled for 30 min in 80 ml 5% SDS. After the samples cooled, they were pelleted (14,000 rpm, 25° C., 1 h) and washed six times by pelleting (14,000 rpm, 25° C., 1 h) from 50 ml water aliquots to remove the SDS. The samples were resuspended in 1 ml PBS, treated with α-amidase (100 μl, 2 mg/ml stock in 50% glycerol, Sigma A-6380) and incubated at 37° C. with shaking for 2 h. To cleave proteins attached to the cell wall, α-chymotrypsin (100 μl, 3 mg/mL in 50% glycerol, Sigma C3142) was added, and the samples were incubated at 37° C. with shaking overnight. An additional aliquot of α-chymotrypsin (100 μl) was added, and the samples were digested for an additional 4 h. To remove the proteins, SDS was added to a final concentration of 1%, and the samples were incubated at 95° C. for 1 h. After cooling, the samples were again pelleted (14,000 rpm, 25° C., 1 h) and washed with water repeatedly (4×25 ml) to remove the SDS. The final peptidoglycan (PG) samples were resuspended in 500 μL 0.02% azide and stored at 4° C.

Mutanolysin Digestion and Analysis

The PG composition was analyzed by LC/MS as previously described (Lebar et al., 2013). The method was also used to analyze LPS samples. The glycosyl hydrolase mutanolysin liberated DPP and disaccharide tetrapeptide from LPS*. Aliquots (40 μl) of PG (from MG1210 and MG1211) and LPS (from MG1210 and MG1211) were incubated with mutanolysin (10 U, 2.5 μl, 4000 U/ml, Sigma M9901, stored at −20° C. in 50 mM TES, pH 7.0, 1 mM MgCl2, 10% glycerol) in 50 mM sodium phosphate buffer (pH 6.0, 100 μl total volume) at 37° C. with shaking overnight. Another aliquot of mutanolysin (10 U, 2.5 μl) was added, and the mixture was incubated at 37° C. with shaking for 3 h. Insoluble particles were separated by centrifugation (16,000×g). The supernatant, containing soluble fragments, was treated with sodium borohydride (10 mg/ml in water, 100 μL) at room temperature for 30 min. Phosphoric acid (20%, 12 μl) was then added to adjust pH to ~4. When bubbling ceased, the samples were lyophilized and re-dissolved in 25 μl water, which was analyzed on LC/MS. LC/MS analysis was conducted with ESI-MS operating in positive mode. The instrument was equipped with a Waters Symmetry Shield RP18 column (5 μm, 3.9×150 mm) with matching column guard. The fragments were separated using the following method: 0.5 ml/min $H_2O$ (0.1% formic acid) for 5 min followed by a gradient of 0% ACN (0.1% formic acid)/$H_2O$ (0.1% formic acid) to 20% ACN (0.1% formic acid)/$H_2O$ (0.1% formic acid) over 40 min.

Surface Plasmon Resonance Analysis

Purified LPS (0.5 mg/ml) from strains MG1210 or MG1211 were extruded in 20 mMTris/HCl pH 8, 150 mM NaCl and immobilized on poly-L-lysine coated CM3 Biacore chips on the active and reference channel, respectively (Malojčić et al., 2014). All experiments were performed using a Biacore X100 instrument at 25° C. at a flow rate of 10 μl/min with 20 mMTris/HCl pH 8, 150 mM NaCl buffer. Different concentrations of vancomycin were injected for 400 s and dissociation was recorded for another 500 s to return to baseline. No binding was observed to the reference channel. The equilibrium signal in the difference channel was fitted to $f=Bmax*abs(x)/(K_d+abs(x))$ with $R^2=0.88$. Standard deviation was measured for 0.6 μM and 1.2 μM vancomycin in triplicate and did not exceed 1 RU.

Assessment of Vancomycin Binding Ability

Figure 13:
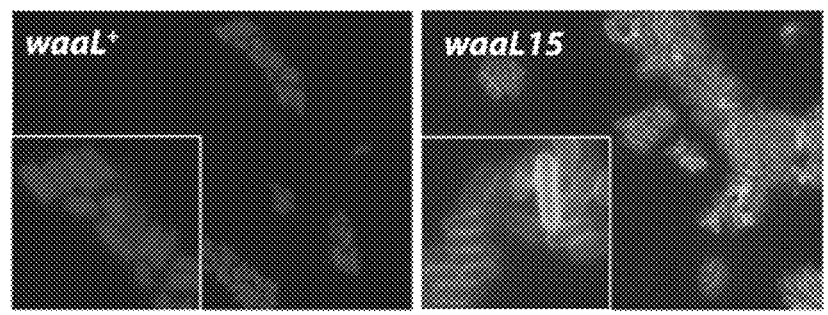
FIG. 13 shows fluorescence microscopy images of waaL+ and waaL15.

The ability of purified LPS* to bind vancomycin in vitro was assessed. LPS* was immobilized on a carboxymethylated dextran (CM3) chip and surface plasmon resonance was used to monitor interactions with differing concentrations of vancomycin. The specific binding of vancomycin to LPS* was measured and a $K_d=0.48±0.08$ μM was obtained (See FIGS. 9-12), which is comparable to a reported $K_d$ for vancomycin-lipid II interactions invesicles (Al-Kaddah et al., 2010). Clearly, LPS* molecules include high affinity binding sites for vancomycin. The ability of LPS* to directly bind vancomycin suggested a possible resistance mechanism, namely that vancomycin is titrated outside the cell. To test this hypothesis, weperformed live cell microscopy using a fluorescent vancomycin-BODIPY. A wild-type strain background with an intact OM that prevents the influx of vancomycin was used, to avoid labeling intracellular sites of PG synthesis. Indeed, waaL+ cells could not be fluorescently labeled (See FIG. 13). On the other hand, circumferential labeling of waaL15 bacteria was readily detected, confirming the presence of accessible D-Ala-D-Ala residues at the cell surface (See FIG. 13).

Comparative Analysis of LPS* and LPS

Traditional adjuvants (e.g. aluminum salts) are potently immunogenic but produce a biased immune response. Specifically, these adjuvants are poor at eliciting a TH1 response to vaccine components. Activation of TH1 responses is important for generating protective antibacterial and antiviral immunity against many pathogens. It is established that the adjuvant effect of LPS produces a TH1-biased immunity. It is also established that LPS-stimulated immune signaling pathways are synergistically activated when provided with additional stimulation with NOD ligands (PG components). By utilizing reporter human cell lines to quantify the strength of immune activation, including activation via TLR4/MD2, NOD1 and NOD2 receptors, the LPS* immune response can be compared to LPS via transcriptomic analysis. The production of immune effector molecules (including cytokines and chemokines) can be characterized using commercially available protein detection assays. It is expected that LPS* will provide more robust immune activation, or result in a distinct profile of immune responses (e.g. biased to TH1-type immunity) and/or distinct production of effector molecules (including cytokines and chemokines) in comparison to LPS, owing to activation of TLR4 and NOD1/2 signaling.

Assessing the Adjuvant Properties of LPS* and Derivative Molecules

The ability of LPS* and its derivatives to elicit protective immunity can be assessed by using these molecules as part of an adjuvant formulation in vaccinations or using model antigens. In one example, mice can be immunized against the ovalbumin antigen by vaccination with formulations where the adjuvant is either an LPS* derivative, or an LPS derivative or alum. The immune response of these mice to vaccinations can be assessed and compared. In another example, the ability of LPS* to elicit protective immunity can be assessed using model pathogens. Mice can be immunized against pathogen antigens by vaccinations formulated with LPS*-based, LPS-based, or alum-based adjuvants. Mice can then be challenged with the pathogen and survival will be recorded and compared to LPS. It is expected that LPS* and its derivatives will provide more robust immunity or result in an altered immunity that improves the efficacy of immunization, compared to LPS and its derivatives.

What is claimed is:

1. A glycoform of lipopolysaccharide modified with a peptidoglycan cell wall fragment produced from an *E. coli* strain carrying a F332S substitution in the O-antigen ligase, such that the glycoform of lipopolysaccharide is bound to a disaccharide with a peptide stem originating from a peptidoglycan precursor molecule.

2. The glycoform of lipopolysaccharide of claim 1, wherein the lipopolysaccharide glycoform is capable of displaying antibiotic-specific binding sites at a cell surface.

3. The glycoform of lipopolysaccharide of claim 2, wherein the antibiotic is vancomycin.

4. The glycoform of lipopolysaccharide of claim 1, wherein the lipopolysaccharide glycoform is capable of activating at least one immune signaling receptor within a human body.

5. The glycoform of lipopolysaccharide of claim 4, wherein the at least one receptor is a TRL4 receptor.

6. The lipopolysaccharide glycoform of claim 4, wherein the at least one receptor is a MD2 receptor.

7. The glycoform of lipopolysaccharide of claim 4, wherein the at least one immune signaling receptor is a NOD1 receptor.

8. The lipopolysaccharide glycoform of claim 4, wherein the at least one receptor is a NOD2 receptor.

9. The glycoform of lipopolysaccharide of claim 1, wherein the lipopolysaccharide glycoform is capable of activating at least one signaling pathway within a human body.

10. The glycoform of lipopolysaccharide of claim 9, wherein the at least one signaling pathway is the TRIF pathway.

11. The lipopolysaccharide glycoform of claim 9, wherein the at least one signaling pathway is the TRAM pathway.

12. A glycoform of alipopolysaccharide (LPS) derivative modified with a peptidoglycan cell wall fragment produced from an *E. coli* strain carrying a F332S substitution in the O-antigen ligase, such that the glycoform of the LPS derivative includes at least one additional sugar.

\* \* \* \* \*

UNITED STATES PATENT AND TRADEMARK OFFICE
CERTIFICATE OF CORRECTION

PATENT NO. : 10,525,126 B2
APPLICATION NO. : 15/586781
DATED : January 7, 2020
INVENTOR(S) : Thomas J. Silhavy et al.

Page 1 of 1

It is certified that error appears in the above-identified patent and that said Letters Patent is hereby corrected as shown below:

In the Claims

In Claim 12, Column 16, Line 48, delete "0-antigen ligase" and insert: --O-antigen ligase--

Signed and Sealed this
Eighteenth Day of February, 2020

Andrei Iancu
*Director of the United States Patent and Trademark Office*